United States Patent [19]

Login et al.

[11] Patent Number: 4,719,287

[45] Date of Patent: Jan. 12, 1988

[54] HIGHER ALKYL PYRROLIDONE EXTRACTANTS FOR WATER SOLUBLE PHENOLIC OR CARBOXYLIC ANTIBIOTICS

[75] Inventors: Robert B. Login, Oakland; Ratan K. Chaudhuri, Butler, both of N.J.

[73] Assignee: GAF Corporation, Wayne, N.J.

[21] Appl. No.: 13,839

[22] Filed: Feb. 12, 1987

Related U.S. Application Data

[63] Continuation-in-part of Ser. No. 879,776, Jun. 27, 1986, abandoned.

[51] Int. Cl.$^4$ .................... C07K 5/12; C07D 407/00; C07H 15/24; A61K 35/00
[52] U.S. Cl. .................................. 530/317; 540/220; 540/346; 549/414; 536/6.4; 424/115; 435/803
[58] Field of Search ............... 540/220, 346; 549/414; 536/6.4; 424/115; 435/803; 530/317

[56] References Cited

U.S. PATENT DOCUMENTS 3,008,955 11/1961 Johnson et al. ............... 540/346
3,884,763 5/1975 Celmer et al. ................. 435/803

OTHER PUBLICATIONS

Chem. Abstr., vol. 106, (1987), 125894.
Chem. Abstr., vol. 100, (1984), 70300.
Chem. Abstr., vol. 95, (1981), 12767.
Chem. Abstr., vol. 83, (1975), 79068.

*Primary Examiner*—Delbert R. Phillips
*Attorney, Agent, or Firm*—Marilyn J. Maue; Joshua J. Ward

[57] ABSTRACT

The extraction of water soluble antibiotics containing a phenolic or carboxylic group from an aqueous solution or fermentation broth using a N—$C_8$—$C_{14}$ alkyl pyrrolidone extractant and the process involving the extraction of said antibiotic.

19 Claims, No Drawings

HIGHER ALKYL PYRROLIDONE EXTRACTANTS FOR WATER SOLUBLE PHENOLIC OR CARBOXYLIC ANTIBIOTICS

This application is a continuation-in-part of co-pending U.S. patent application Ser. No. 879,776, filed June 27, 1986, now abandoned, entitled "SURFACE ACTIVE LACTAMS".

In one aspect, the invention relates to an extractant or extractant aid for isolating normally solid, polar antibiotics from an aqueous solution or fermentation broth. In another aspect, the invention relates to the process of effecting said extraction.

BACKGROUND OF THE INVENTION

An important consideration in the recovery of an antibiotic from aerobic or anaerobic industrial fermentation processes is the nature and properties of the micro-organism to be recovered. Non-polar antibiotics which are insoluble in water are more easily recovered by the use of a large number of water insoluble solvents such as chloroform, methylene chloride, ethyl acetate etc.; however, antibiotics such as the penicillins, tetracyclin, rifampicin, and doxorubicin, which are polar and which are present in relatively low concentrations, e.g. 0.5–5% by weight, pose a more difficult challenge. Such polar, water soluble compounds require an extraction agent of high efficiency for their recovery.

Basically the fermentation process involves inoculating a sterilized or pasteurized nutrient medium contained in a fermentor with between about 1 wt % and about 10 wt % of a culture of the desired microorganism, or its enzyme usually in the logarithmic phase of its life cycle. The temperature and pH of the fermentation broth is closely controlled during catabolism to between about 20° and 40° C. and 6 to 8 pH. After a period of from about 3 days to about 3 weeks the desired antibiotic is produced. Antibiotics, thus produced include macrolides, polyenes, polypeptides, penicillins, tetracyclines, and the like. The desired fermentation product contained in the broth, together with nutrients, such as sugars, alcohols and salts as well as original and often mutant microorganism forms, then enters the product recovery stage. Heretofore, recovery has been accomplished by a series of time consuming chemical and physical treatments which include chilling, heating, distillation, extraction, evaporation, crystallization, solubilization and recrystallization in order to isolate a substantially pure antibiotic useful in human and animal therapy. It is evident that the recovery is considerably more costly than the preceding fermentation and improved methods for product recovery have long been saught for process economy and commercialization.

Accordingly, it is an object of this invention to provide an improved and commercially feasible process for the recovery of water soluble, and other polar antibiotics from aqueous fermentation broths and to supply an extractant composition suitable for isolating said antibiotic products from a fermentation broth.

Another object is to provide a select group of chemical compounds which have the unique property of extracting desired antibiotics.

These and other objects of the invention will become apparent from the following description and disclosure.

In accordance with the present invention, there is provided a group of water insoluble or partially water soluble lactams for antibiotic extraction having the formula

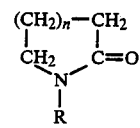

wherein n is an integer having a value of from 1 to 3 and R is alkyl having from 8 to 14 carbon atoms. These extraction agents have the unique capability of extracting 90% or more of the polar, antibiotics of this invention from a fermentation broth.

The chain length of the R group attached to heterocyclic nitrogen is critical to the operation of the present invention since alkyl groups below $C_8$ are water soluble and thus prevent phase separation of the product contained in the fermentation broth, an essential feature of the present invention. Alkyl groups above $C_{14}$ are solid and cannot be utilized for extraction.

Of the above extraction agents, those having a relatively low critical micelle concentration of between about $1 \times 10^{-3}$ and $1 \times 10^{-4}$ mole per liter of water, and wherein R is $C_8$–$C_{12}$ alkyl and n is one, are preferred. Most preferred for extraction of water soluble antibiotics in N-octyl-2-pyrrolidone.

The extraction agent of this invention can be any of the above described lactams employed individually or in admixtures to suit the purposes of a specific operation. Also, the lactam extractant can be used in an undiluted state or in solution with a water insoluble solent, such as butyl acetate, ethyl acetate, n-butanol, toluene, methylene chloride, chloroform, and the like, when added to the fermentation broth. When solutions of the lactams are employed, concentrations as low as 2 wt % of lactam in solvent can be employed; however, from the standpoint of economics and concentration control, it is preferred to employ the present lactam extractants in an undiluted state.

The microorganisms of this invention which undergo aerobic and anaerobic fermentation to provide valuable polar, products containing a phenolic and/or carboxylic group include animal forms such as slime molds, protozoa, bacteria, fungi, lichens and algae.

The following Table I provides some specific examples of microorganisms used in the preparation of the present products.

TABLE I

| Producer Organism | Antibiotic Compound | Chemical Type |
|---|---|---|
| Penicillium Chrysogenum | Penicillin V | β-Lactam |
| Penicillium Chrysogenum | Penicillin G | β-Lactam |
| Cephalosporium acremonium | Cephalosporin C | β-Lactam |
| Streptomyces peuceticus var. caesius | Doxorubicin | Anthracycline |
| Streptomyces peuceticus, S. coeruleorubidus | Daunorubicin | Anthracycline |
| Streptomyces nodosus | Amphotericin B | Polyene |
| Streptomyces griseus | Streptomycin | Aminoglycoside |
| Streptomyces aureofaciens | Tetracyclins | Polypeptide |
| Streptomyces orientalis | Vancomycin | Glycopeptide |
| Streptomyces lasaliensin | Lasalocid | Polyether |
| Nocardia mediterranei | Rifamicins | Ansamycin |

Of the above types, the microorganisms streptomyces, penicillium, cephalosposium, and norcardia which produce commercially valuable products are preferred.

Generally the process of this invention is carried out at a temperature of between about 20° C. and about 50° C. under a pressure of from about 14 to about 50 psig, preferably at a temperature between about 25° and 35° C. and ambient pressure. The process involves filtration of the fermentation broth to remove water insoluble materials such as mycelium, and adding between about 0.2% and about 10% by weight of the present extraction to the filtrate. Preferably, when the lactam of the present invention is the sole extractant in the process, between about 1% and about 5% by weight is added to the broth. However, it is within the scope of this invention to employ the present lactam as a supplementary extractant to a conventional extraction agent which may be used in the system. In the later case as little as 0.2 wt% of the present lactam can be used to provide greatly improved results. In either case, the total amount of extractant introduced into the recovery process should be between about 1% and about 10% by weight, preferably between about 1.5% and about 5% by weight, with respect to the fermentation broth. Generally the weight ratio of extractant to product is maintained between about 500:1 and about 10:1, preferably between about 100:1 and about 20:1.

In the case of water soluble products, after uniform incorporation of the extractant, the broth separates into an organic phase and an aqueous phase. The organic phase containing the desired antibiotic can be recovered in at least 90% purity in a single separation step. The extractant with desired product can be utilized as the product of the process, or the organic phase can be subjected to further treatment for removal and recovery of lactam.

Alternatively, the lactam extractant can be removed from the antibiotic by chromatography using normal phase or reverse phase silica gel chromatography, gel filtration counter-current distribution, high pressure liquid chromatography etc. using a wide variety of solvents or solvent mixtures, namely hexane, toluene, methylene chloride, chloroform, ethyl acetate or butyl acetate. The lactam can then be recycled to the extraction zone in the system. This lactam recovery and recycled operation provides for an economical and continuous process.

The principles of the present invention can be applied to fermentations of a wide variety of polar materials. Thus the products which can be extracted by the present process include any of the polar, water soluble or water insoluble antibiotics, organic acids, vitamines, nucleosides, peptides, nucleotides, amino acids and miscellaneous products listed on pages 865-868, Volume 9 of Kirk Othmer's Encyclopedia of Chemical Technology, 5th Edition. Preferred of these are the antibiotics containing a phenolic and/or carboxylic group such as penicillins, cephalosporins, anthracyclins, rifampicins, vancomycins, tetracyclins etc.

A major advantage of the above process is that the present lactams can be used to recover 90% or more of a water soluble product from a product lean broth without resorting to distillation and subsequent evaporation and crystallization steps. Thus, the present process materially reduces the process time and cost of conventional recovery processes now in use.

Having thus described the invention, reference is now had to the following examples which illustrate preferred embodiments but which are not to be construed as limiting to the scope of the invention as more broadly defined above and in the appended claims.

EXAMPLES 1-5

Aqueous 100 ml solutions of the following antibiotics were prepared in 1 liter glass flasks. To these aqueous solutions was added N-dodecyl-2-pyrrolidone in the amounts indicated in Table II, After the addition, the contents of the flasks were heated to 30° C. for 5 minutes whereupon two liquid layers separated, i.e. an upper organic layer containing antibiotic and N-dodecyl-2-pyrrolidone and a lower water layer. The layers were separated and weighed for antibiotic content which was determined by UV absorption.

TABLE II

| Example No. | grams of Antibiotic in water | pH of Antibiotic soln. | % N—$C_{12}$ P added to soln. | % Antibiotic in soln. | % Antibiotic in N—$C_{12}$ P layer |
|---|---|---|---|---|---|
| 1 | 0.02 g Lasalocid | 3 | 2 | 0.02 | >80 |
| 2 | 0.02 g Rifampicin | 6.5 | 2 | 0.02 | >80 |
| 3 | 0.02 g Tetracyclin | 5.7 | 6 | 0.02 | ~50 |
| 4 | 0.025 g Vancomycin | 10.6 | 2 | 0.025 | ~50 |
| 5 | 0.05 g Vancomycin | 10.6 | 4 | 0.05 | ~55 |

EXAMPLES 6-8

One hundred grams of each of the following solvents were employed to dissolve each of the following antibiotics. The amount in grams of antibiotic which dissolved in each solvent is reported in following Table III.

TABLE III

| | | solvents g. of Antibiotic Dissolved in 100 g. Solvent | | | |
|---|---|---|---|---|---|
| Example No. | Antibiotic | NBUOAc[1] | BuOH[2] | $C_8$ alkyl pyrrolidone | $C_{12}$ alkyl pyrrolidone |
| 6 | Rifampicin | 0.54 | <0.30 | 3.34 | 2.0 |
| 7 | Penicillin V | 1.37 | 2.86 | 42.22 | 24.11 |
| 8 | Tetracyclin | <0.55 | 1.8 | 6.25 | 3.23 |

[1]n-butylacetate
[2]n-butanol

EXAMPLES 9-13

The procedure described for Examples 1-5 was repeated to provide aqueous solutions of the antibiotics reported in Table IV,. In each case 2% of the indicated extraction agent was added to the antibiotic solution.

The amount of antibiotic extracted is reported in Table IV.

TABLE IV

| Example No. | g. of Antibiotic in $H_2O$ | pH of Antibiotic soln. | % Antibiotic in $H_2O$ | % Antibiotic extracted |
|---|---|---|---|---|
| 9 | 0.02 g. Rifampicin | 6.5 | 0.02 | >80 |
| 10 | 0.02 g. Lasalocid | 3.0 | 0.02 | >80 |
| 11 | 0.02 g. Penicillin V | 3.4 | 0.02 | >80 |
| 12 | 0.02 g. Penicillin V | 3.4 | 0.02 | >80 |
| 13 | 0.01 g. Doxorubicin | 5.8 | 0.01 | >80 |

(a) N—dodecyl-2-pyrrolidone
(b) N—octyl-2-pyrrolidone

EXAMPLE 14

A Penicillin V containing fermentation broth (40 Kg in 1 liter of broth) is filtered on a vacuum filter to remove the mycellium. In a continuous process, the resulting Penicillin V containing filtrate is extracted at 0°-5° C. in an extraction zone with N-octyl-2-pyrrolidone (100 ml) using a continuous counter-current centrifugal extractor. The effluent from the extractor separates into a lower aqueous layer and an upper penicillin rich N-octyl pyrrolidone layer. The upper layer is drawn off and is then treated with active charcoal to remove pigments and other impurities. The charcoal is separated from the extract by filtration and washed with small amount of N-octyl-2-pyrrolidone (10 ml). The Penicillin V is crystallized as an alkali metal salt e.g. a sodium salt by addition of alkali metal acetate or bicarbonate, e.g. sodium acetate to the pyrrolidone phase. The Penicillin V sodium salt crystals are collected on a vacuum filter. The filtrate, i.e. recovered N-octyl-2-pyrrolidone is recycled to the extraction zone for additional extraction of penicillin.

The penicillin salt crystals are washed and predried with anhydrous isopropyl alcohol to remove residual impurities (pigments, unused potassium or sodium acetate etc.). The crystal slurry is then filtered, washed with fresh anhydrous solvent and hot air dried. The penicillin salt at 99.5% purity is obtained in 85% recovery.

EXAMPLE 15

The procedure described for Example 14 is repeated except that the extracting solvent used is a cosolvent mixture of n-butyl acetate and N-octyl-2-pyrrolidone (90:10, 200 ml). The penicillin salt product is recovered in the same percent amount and purity.

It is to be understood that the other extractants of this invention or their intermixtures or mixtures with conventional extractants can be substituted for N-octyl-2-pyrrolidone in Example 14 to provide the improved process of this invention.

EXAMPLE 16

Aqueous 300 ml solutions (A–D) of the following compounds were made up
A. Igepal CO-210, an ethoxylated (Av 1.5) nonyl phenol
B. Antarox BL-214, a linear aliphatic polyether (EO=Av. 5, PO=Av. 8; Av. MW=582)
C. Antarox BL-225, a linear aliphatic polyether (EO=Av. 5, PO=Av. 4; av. MW=596)
D. N-cyclohexyl-2-pyrrolidone
and 100 ml of each solution (A–D) was used to extract each of the following antibiotics from aqueous solutions
Rifampicin
Penicillin V and
Tetracyclin Solutions A formed emulsions with the antibiotics; thus, no phase separation occurred and no extraction could be made.

Solutions B produced suspensions of the antibiotics, thus preventing phase separation and extraction by the process of this invention.

Solutions C produced homogeneous clear solutions of the antibiotics thus preventing extraction by the present process.

Finally, solutions D also formed clear solutions with the antibiotics. No phase separation occurred; accordingly, extraction by the present process could not be carried out.

It is to be understood that many modifications and variations in the above examples can be made in accordance with the foregoing description and disclosure without departing from the scope of this invention. Particularly any of the fermentation products containing a phenol and/or a carboxylic group can be substituted in the above examples 1-15 to provide the improvements of this invention. Also, any of the foregoing N-alkyl-pyrrolidone extraction agents, their intermixtures or mixtures with conventional extractants can be substituted in Examples 1-15 to provide the benefits described herein.

What is claimed is:

1. An aqueous composition comprising an aqueous fermentation broth having a pH of from 6 to 8 and containing (a) a fermentation product in an amount not more than 10% by weight of said broth said fermentation product having a phenolic and/or a carboxylic group and (b) between about 0.2% and about 10% by weight based on said broth of a N-alkyl-lactam extraction agent having the formula

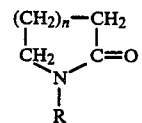

wherein n is an integer having a value of from 1 to 3 and R is alkyl having 8 to 14 carbon atoms.

2. The composition of claim 1 wherein said fermentation product is an antibiotic.

3. The composition of claim 2 wherein the total amount of extraction agent in said fermentation broth is between about 1% and about 10% by weight.

4. The composition of claim 3 wherein said extraction agent is a N-alkyl-2-pyrrolidone.

5. The composition of claim 4 wherein said composition contains at least 0.2% by weight of said N-alkyl-pyrrolidone extraction agent and between about 0.8% and about 9.8% by weight of a conventional extraction agent for said antibiotic.

6. The composition of claim 4 wherein said composition contains between about 1.5% and about 5% by weight of said N-alkyl-2-pyrrolidone and said N-alkyl-2-pyrrolidone is the sole extraction agent in the composition.

7. The composition of claim 2 wherein said antibiotic is selected from the group consisting of rifampicin, cephalosporin, penicillin, tetracyclin, vancomycin, lasalocid and doxorubicin.

8. The composition of claim 2 wherein the antibiotic is water soluble.

9. The composition of claim 2 wherein the antibiotic is water insoluble.

10. The process of contacting the fermentation product of claim 1 in said fermentation broth with an effective fermentation product extracting amount of a N-alkyl lactam having the formula

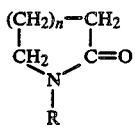

wherein n is an integer having a value of from 1 to 3 and R is alkyl having from 8 to 14 carbon atoms.

11. The process of claim 10 wherein the fermentation product is an antibiotic and said N-alkyl lactam is an N-alkyl-2-pyrrolidone.

12. The process of claim 11 wherein said antibiotic is water soluble.

13. The process of claim 11 wherein the fermentation broth is separated into an organic liquid phase and an aqueous phase after contacting said antibiotic containing fermentation broth with said N-alkyl-2-pyrrolidone and wherein said orgainc phase containing antibiotic and said N-alkyl-2-pyrrolidone is recovered as the product of the process.

14. The process of claim 13 wherein the antibiotic containing fermentation broth contacted with said N-alkyl-2-pyrrolidone is heated to a temperature below about 50° C. before said separation into liquid phases.

15. The process of claim 10 wherein the effective fermentation product extracting amount of said N-alkyl lactam is between about 0.2% and about 10% by weight based on said fermentation broth.

16. The process of claim 15 wherein said N-alkyl lactam is an N-alkyl-2-pyrrolidone containing 8 to 14 carbon atoms, said N-alkyl-2-pyrrolidone is the sole extracting agent employed to extract said fermentation product and the amount of said N-alkyl-2-pyrrolidone employed to effect said extraction is between about 1.5% and about 5% by weight of said fermentation broth.

17. The process of claim 11 wherein the fermentation broth is separated into an organic liquid phase and an aqueous phase after contacting said antibiotic with said N-alkyl-2-pyrrolidone in a separation zone, the organic phase containing antibiotic and N-alkyl-2-pyrrolidone is separated from the aqueous phase and said N-alkyl-2-pyrrolidone is separated from antibiotic in the organic phase, the separated N-alkyl-2-pyrrolidone is eluted with an inert organic solvent, the resulting mixture is distilled to recover N-alkyl-2-pyrrolidone and the N-alkyl-2-pyrrolidone is recycled to said separation zone as extractant for said antibiotic.

18. The process of claim 17 wherein said N-alkyl-2-pyrrolidone is N-octyl-2-pyrrolidone.

19. The process of claim 17 wherein said N-alkyl-2-pyrrolidone is N-dodecyl-2-pyrrolidone.